June 17, 1975 C. H. FISCHER Plant Pat. 3,732
GLADIOLUS PLANT
Filed March 18, 1974
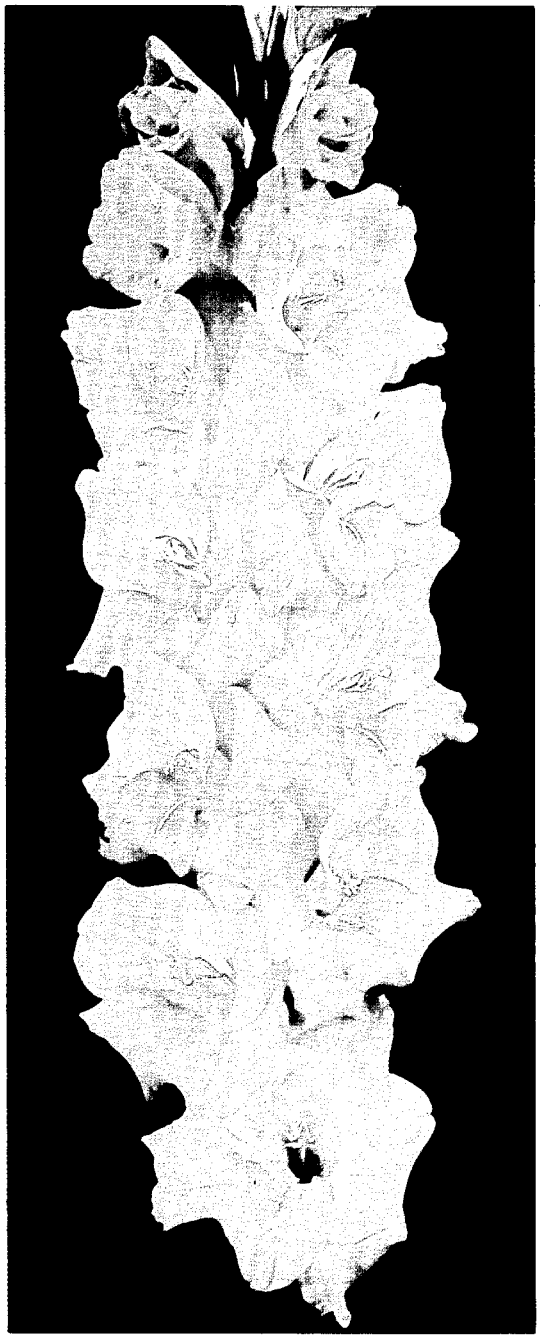

United States Patent

Plant Pat. 3,732
Patented June 17, 1975

3,732
GLADIOLUS

Carl H. Fischer, St. Charles, Minn., assignor to Selected Glads, Inc., New Albany, Ind.

Filed Mar. 18, 1974, Ser. No. 452,290
Int. Cl. A01h 5/00
U.S. Cl. Plt.—85 1 Claim This invention relates to a new and distinct variety of gladiolus plant.

This new gladiolus plant was originated by me by crossing a seed parent known as "Christmas Red" (Pat. No. 2363) with a pollen parent known as "Valeria."

The improved variety resulting from this breeding is evidenced by the following unique combination of characteristics which are outstanding therein and which distinguish my new variety from its parents, as well as from other varieties of which I am aware:

First: A color combination so unique and distinctive in its deeper color that no other variety resembles mine
Second: A variety which is early in blooming.

In addition to these major characteristics my variety is also endowed with the following characteristics:

1. A robust vigor, vibrant red color and ability to grow marketable spikes even from small bulbs.
2. Good bud count opening many florets at one time.
3. A stem free from crooking, extremely uniform spikes are formed, from one plant to another.
4. Admirable and consistent growth habits.
5. Excellent propagative powers.
6. Strong plant relative to weather and wind.

I have asexually reproduced the new variety by cormels through several generations in Minnesota, and succeeding generations have established that the distinguishing characteristics of the variety held true. By natural increase from cormels through several generations its color and other characteristics have proven to be permanently fixed.

The accompanying drawing shows a typical specimen of a flower spike of the new variety, with the flowers in varied stages of growth. Some are shown as partially opened buds and others as fully opened buds. The colors depicted are as nearly true as is possible to achieve in this type of reproduction.

The following is a detailed description of my new variety, with color terminology in accordance with the Horticultural Colour Charts issued by the British Colour Council and the Royal Horticultural Society, except where general color terms of ordinary dictionary significance are obvious.

*Plant*

Growth
Healthy, robust and precocious: excellent propagator, attaining a height of 66 inches.

Blooming Habit
The flower blooms early. Under normal conditions, in the northern regions of the United States, the first bloom appears approximately 75 days after planting, with about 6–7 florets showing color at one time.

Stems
*Form*: Fairly tall and straight.
*Diameter at base*: About ½ inch.
*Color at base*: Deep rose.

Foliage
Above the ground the plant has deep green, broad and stiffly upright leaves with medium to low breaking foliage. The average leaf is 2 to 2¼ inches wide at the base, and the foliage excluding the flower spike is 30–33 inches high.

Disease Resistance
The variety has been found to be unusually resistant to the usual gladiolus plant diseases of a bacterial, viral or fungoid genesis.

Corms
Mature bulbs are smooth, round and having a high crown with firmly attached husks which have a purple cast.
*Color of flesh*: Red with a pencil line of red where the husk is attached to the bulb.

*Flower*

Spike
*Form and size*: Tall and straight with a flowerhead length of 24 to 30 inches, regularly carrying 24 to 26 buds.

Bud
*Size*: About 3 to 3½ inches long when opening.
*Opening*: After first blooming 6–7 show color at one time thereafter.

Flower
*Arrangement*: Flowerhead of the new variety has a formal placement.
*Size*: Individual florets average about 5½ to 6 inches in diameter.
*Form*: Florets are slightly rounded and flat.
*Keeping qualities*: The flowers are long lasting and open exceptionally well when cut in tight buds.

Petals
*Shape*: Somewhat round.
*Size*: Upper petals about 2 to 2½ inches wide. Lip petals about 1 to 1½ inches wide.
*Aspect*: Substance is average and being somewhat rounded.
*Fragrance*: None.
*Color*: The petals of this variety are unusual in color being predominantly and uniformly red colored, Dutch Vermilion #717, with a blotch on the lip of Blood Red 820.

*Reproductive Organs*

Stamens
*Color*: Pale Dutch Vermilion, #717/3.

Pistils
*Color*: The stem of the reproductive organs is white coming out of the calyx and #717/3 Pale Dutch Vermilion where stamens and pistil develop.

*Growth*

Locality where grown and observed: St. Charles, Minn.
Propagation: Holds its distinguishing characteristics through succeeding propagations from cormels.

It can be seen that this variety is unique in its red color with a lip blotch, and in the fact that it blooms early, in about seventy-five days.

What I claim is:

1. A new and distinct variety of gladiolus plant, substantially as herein shown and described, characterized particularly as to novelty by the unique combination of its unique color, which is predominantly red, and its early blooming habit.

No references cited.

ROBERT E. BAGWILL, Primary Examiner